US00PP16463P2

(12) United States Plant Patent
Evers

(10) Patent No.: US PP16,463 P2
(45) Date of Patent: Apr. 18, 2006

(54) HYBRID TEA ROSE PLANT NAMED 'TAN01994'

(50) Latin Name: *Rosa hybrida*
Varietal Denomination: TAN01994

(75) Inventor: Christian Evers, Uetersen (DE)

(73) Assignee: Rosen Tantau Mathias Tantau Nachfolger, Ueterwen (DE)

( * ) Notice: Subject to any disclaimer, the term of this patent is extended or adjusted under 35 U.S.C. 154(b) by 46 days.

(21) Appl. No.: 10/975,688

(22) Filed: Oct. 27, 2004

(51) Int. Cl.
*A01H 5/00* (2006.01)

(52) U.S. Cl. ..... Plt./131

(58) Field of Classification Search ..... Plt./131
See application file for complete search history.

*Primary Examiner*—Anne Marie Grunberg
*Assistant Examiner*—Annette H Para
(74) *Attorney, Agent, or Firm*—Klarquist Sparkman LLP

(57) ABSTRACT

Hybrid tea rose plant substantially as herein shown and described, characterized particularly by its red and silvery-white flowers and its good bud-to-stem ratio.

1 Drawing Sheet

Genus and species: *Rosa hybrida.*
Varietal denomination: 'TAN01994'.

SUMMARY OF THE INVENTION

The present invention relates to a new and distinct variety of hybrid tea rose plant for cut flower production, which was discovered by me as a spontaneous, natural mutation of the rose variety Tan99065 growing in a greenhouse in Uetersen, Germany.

BRIEF SUMMARY OF THE INVENTION

This mutant has an attractive bi-colored flower and has a good bud-to-stem ratio.

Asexual reproduction of this new variety by cuttings, as performed at Uetersen, Germany, shows that the foregoing and all other characteristics and distinctions come true to form and are established and transmitted through succeeding propagations.

COMPARISON WITH PARENT

The parent plant, TAN099065, has red flowers whereas the petals of TAN01944 are red on their upper surfaces and silvery-white on their lower surfaces.

BRIEF DESCRIPTION OF THE ILLUSTRATION

The accompanying illustration shows typical specimens of flowers of this new variety depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parent: TAN099065 (Plant patent application Ser. No. 10/282,787, filed Oct. 28, 2002).

Classification:
*Botanical.*—*Rosa hybrida.*
*Commercial.*—Hybrid Tea.

FLOWER

Observations made from plants of two years of age grown in a greenhouse environment at Uetersen, Germany.

Blooming habit: Continuous.

Bud:
- *Size.*—About 2.7 cm long and 2.4 cm in diameter when the petals start to unfurl.
- *Form.*—The bud form is blunt.
- *Color.*—When sepals first divide, bud color is Silvery-White Group 155D. When half blown, the upper sides of the petals are Red Group 46A; and the lower sides of the petals are White Group 155A.
- *Sepals.*—Color: Upper Surface: Green Group 144A. Lower Surface: Green Group 144C. Length: 3.4 cm. Width: 0.6 cm. Shape: Pointed-elongate. Surface texture: Rough. There are three normally appendaged sepals. There are five unappendaged sepals with serrated edges.
- *Receptacle.*—Color: Green Group 144C. Shape: Funnel. Size: Medium, about 0.4 cm by 0.4 cm. Surface: Smooth.
- *Peduncle.*—Length: About 5.7 cm. Surface: Smooth. Color: Green Group 144A. Strength: Erect.

Bloom:
- *Size.*—Large. Average open size is about 8.6 cm.
- *Borne.*—Singly.
- *Stems.*—Strength: Normal. Average length is about 60 cm and 0.3 cm in diameter.
- *Form.*—When first open: Flat. Permanence: Retains its form to the end, outer petals curl back.
- *Petalage.*—Number of petals under normal conditions: 39.
- *Color.*—The upper sides of the petals are Red Group 46A. The reverse sides of the petals are White Group 155A. The base of each petal has a Yellow Group 14D spot. The major color on the upper side is Red Group 46A.

*Variegations.*—None.

*Discoloration.*—The general tonality at the end of the first day: Red Group 46A, and at the end of the third day: Red Group 46A.

*Fragrance.*—None.

Petals:

*Texture.*—Leathery.

*Surface.*—Rough.

*Shape.*—Oval.

*Size.*—Width: 5.2 cm. Length: 4.5 cm.

*Margin.*—Smooth. Apex Shape: Pointed. Base Shape: Blunt.

*Form.*—Edges slightly quilled.

*Arrangement.*—Irregular.

*Petaloids.*—Number 22. Color: Same as petals.

*Persistence.*—Petals hang on and dry.

*Lastingness.*—On the plant: Long, about 17 days. As a cut flower: Long, about 15 days.

Reproductive parts:

*Stamens.*—Number: 83. Length: 0.4 cm. Anthers: Length: 0.1 cm. Color: Yellow-Orange Group 22A. Arrangement: Regular around styles. Filaments: Color: Yellow-Orange Group 22B. Length: 0.3 cm. Pollen: Color: Yellow-Orange Group 21A.

*Pistils.*—Number: 112. Length: 4 cm. Styles: Color: Red Group 43A. Length: 0.3 cm. Stigmas: Color: Yellow-Orange Group 22A. Length: 0.1 cm.

*Hips.*—None produced.

PLANT

*Form.*—Pillar.

*Growth.*—Vigorous.

*Mature plant.*—Height: 80 cm at 2 years. Width: 40 cm.

*Rootstock.*—*Rosa* canina.

Foliage: Number of leaflets on normal mid-stem leaves: 5.

*Size.*—Medium (12.2 cm long×8.2 cm wide).

*Quantity.*—Normal.

*Color.*—New foliage: Upper side: Green Group 139A. Lower side: Green Group 137B. Old foliage: Upper side: Green Group 139A. Lower side: Green Group 137B.

Leaflets:

*Size.*—About 8.2 cm long×4.5 cm wide.

*Shape.*—Pointed oval.

*Base shape.*—Blunt.

*Apex shape.*—Pointed.

*Texture.*—Upper side: Smooth.

*Edge.*—Serrated.

*Serrations.*—Single.

*Petiole.*—Color: Green Group 137A.

*Petiole rachis.*—Color: Green Group 139B. Underside: Smooth.

*Stipules.*—Length: 1.1 cm, smooth.

*Auricles.*—Number: 2. Length: 0.2 cm. Shape: Pointed.

*Disease resistance.*—Not tested.

*Pest resistance.*—Not tested.

*Vein color.*—Green Group 144A.

*Venation pattern.*—Pyramidal.

Wood:

*New wood.*—Color: Green Group 144A. Bark: Smooth.

*Old wood.*—Color: Brown Group 183A. Bark: Rough.

Prickles:

*Quantity.*—On main canes from base: 16 per 60 cm stem. On laterals from main canes: 1 per 20 cm.

*Form.*—Hooked downward.

*Length.*—0.5 cm.

*Color when young.*—Purple Group 185A.

*Color when mature.*—Purple Group 177A.

Small prickles:

*Quantity.*—On main stalks: 15 per 30 cm length. Color: When young: Green Group 146C. When mature: Grey-Orange Group 177A.

Winter hardiness: Not tested.

I claim:

1. A new and distinct variety of rose plant of the hybrid tea class, substantially as herein shown and described, characterized particularly by its red and silvery-white flowers and its good bud-to-stem ratio.

* * * * *

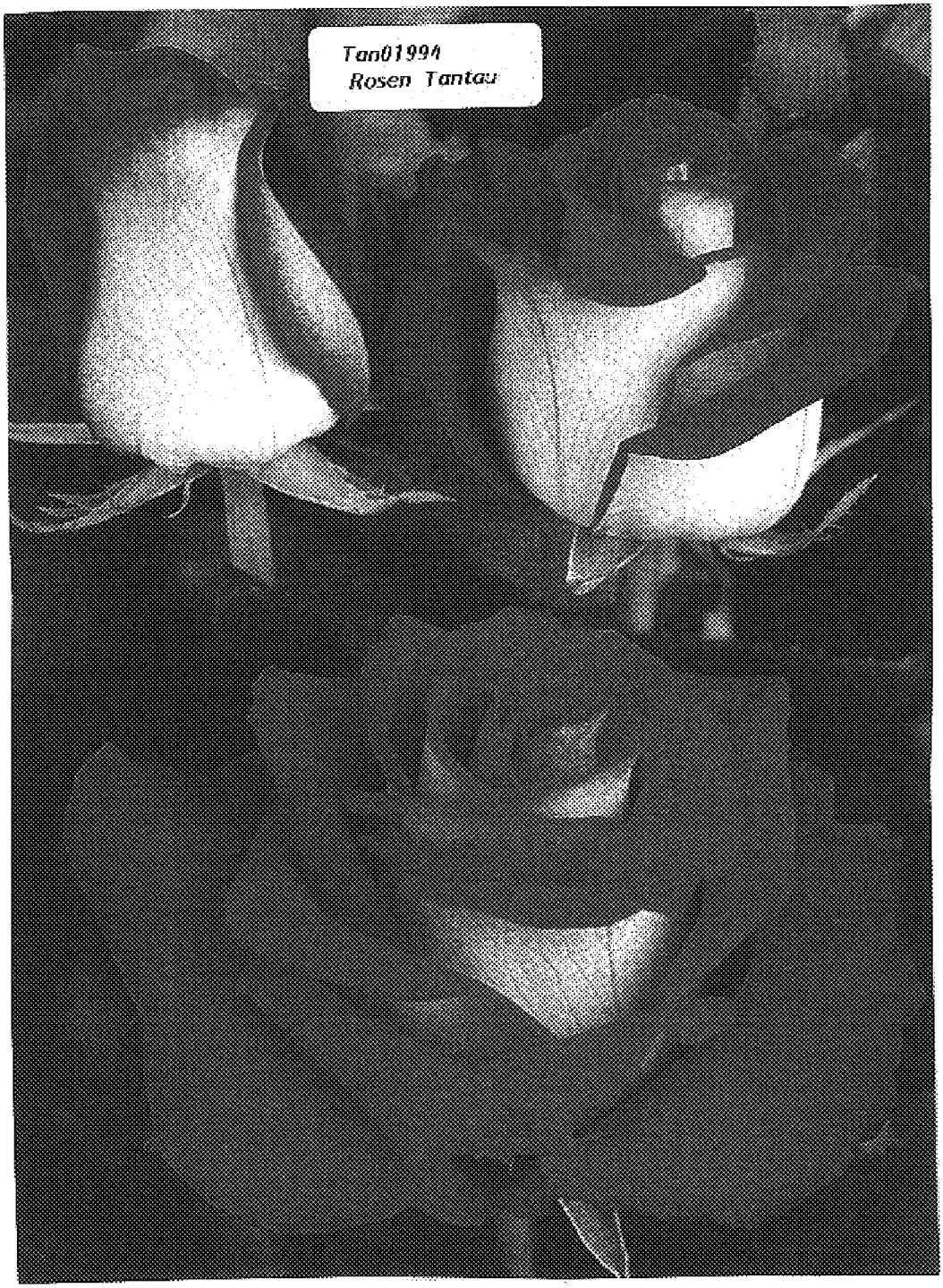
Tan01994
Rosen Tantau